United States Patent
Lewis et al.

(10) Patent No.: US 8,569,558 B1
(45) Date of Patent: Oct. 29, 2013

(54) METALLOPHOSPHATE MOLECULAR SIEVES, METHOD OF PREPARATION AND USE

(71) Applicant: UOP LLC, Des Plaines, IL (US)

(72) Inventors: Gregory J. Lewis, Santa Cruz, CA (US); Lisa M. Knight, Chicago, IL (US); Paulina Jakubczak, Elk Grove Village, IL (US); Justin E. Stanczyk, Arlington Heights, IL (US)

(73) Assignee: UOP LLC, Des Plaines, IL (US)

( * ) Notice: Subject to any disclaimer, the term of this patent is extended or adjusted under 35 U.S.C. 154(b) by 0 days.

(21) Appl. No.: 13/690,078

(22) Filed: Nov. 30, 2012

(51) Int. Cl.
*C07C 2/66* (2006.01)

(52) U.S. Cl.
USPC .......................................... 585/467; 585/455

(58) Field of Classification Search
USPC ................................................. 585/467, 455
See application file for complete search history.

(56) References Cited

U.S. PATENT DOCUMENTS

| 4,310,440 | A | 1/1982 | Wilson et al. |
| 4,440,871 | A | 4/1984 | Lok et al. |
| 4,567,029 | A | 1/1986 | Wilson et al. |
| 4,870,222 | A | 9/1989 | Bakas et al. |
| 4,973,785 | A | 11/1990 | Lok et al. |
| 5,126,308 | A | 6/1992 | Barger et al. |
| 5,157,196 | A | 10/1992 | Crossland et al. |
| 5,157,197 | A | 10/1992 | Cooper et al. |
| 2012/0157741 | A1 | 6/2012 | Cao et al. |

OTHER PUBLICATIONS

Sivasanker et al. "Synthesis of SAPO-35 in non-aqueous gels", Journal of the Chemical Society, 1997, pp. 3411-3415, vol. 93, Issue 18.
Prakash et al., "SAPO-35 Molecular Sieve: Synthesis, Characterization, and Adsorbate Interactions of Cu(II) in CuH-SAP035", Chemistry of Materials, 1998, pp. 932-941, vol. 10.
Mendau, "Synthesis and Characterization of the Elvyne-like Structure SAPO-35 Prepared with Cyclohexylamine as Templating Agent", Crystal Research and Technology, 1993, pp. 1101-1107, vol. 28, Issue 8.
Li, "LEV-zeotype magnesium aluminophosphates with variable Mg/Al ratios", Dalton Transactions, 2012, pp. 6855-6860, vol. 41, Issue 22.
Gatter, "Stability of framework aluminum in the new zeolite UZM-5", Studies in Surface Science and Catalysis, 2004, pp. 1324-1331,vol. 154, Part B.
Smith et al., "Enumeration of 4-connected 3-dimensional nets and classification of framework silicates; the infinite set of ABC-6 nets; the Archimedean and sigma—related nets", American Mineralogist, Aug. 1981, pp. 777-788, vol. 66.

*Primary Examiner* — Thuan D Dang
(74) *Attorney, Agent, or Firm* — Maryann Mass

(57) ABSTRACT

A new family of crystalline microporous metallophosphates designated AlPO-67 has been synthesized. These metallophosphates are represented by the empirical formula $$R^+_r M_m^{2+} E P_x Si_y O_z$$

where R is an organoammonium cation such as the ETMA⁺ or DEDMA⁺, M is a framework metal alkaline earth or transition metal of valence 2+, and E is a trivalent framework element such as aluminum or gallium. The AlPO-67 compositions have the LEV topology and have catalytic properties for carrying out various hydrocarbon conversion processes, and separation properties for separating at least one component.

8 Claims, No Drawings

METALLOPHOSPHATE MOLECULAR SIEVES, METHOD OF PREPARATION AND USE

FIELD OF THE INVENTION

This invention relates to a new family of charged metallophosphate-based molecular sieves designated AlPO-67, which has the LEV topology, and is utilized as the catalytic composite for hydrocarbon conversion reactions, or as a separation material used in separation processes. They are represented by the empirical formula of:

$$R^+_r M^{2+}_m EP_x Si_y O_z$$

where M is a divalent framework metal such as magnesium or zinc, R is an organoammonium cation such as ethyltrimethylammonium and dimethylammonium and E is a trivalent framework element such as aluminum or gallium.

BACKGROUND OF THE INVENTION

Zeolites are crystalline aluminosilicate compositions which are microporous and which are formed from corner sharing $AlO_2^-$ and $SiO_2$ tetrahedra. Numerous zeolites, both naturally occurring and synthetically prepared are used in various industrial processes. Synthetic zeolites are prepared via hydrothermal synthesis employing suitable sources of Si, Al and structure directing agents such as alkali metals, alkaline earth metals, amines, or organoammonium cations. The structure directing agents reside in the pores of the zeolite and are largely responsible for the particular structure that is ultimately formed. These species balance the framework charge associated with aluminum and can also serve as space fillers. Zeolites are characterized by having pore openings of uniform dimensions, having a significant ion exchange capacity, and being capable of reversibly desorbing an adsorbed phase which is dispersed throughout the internal voids of the crystal without significantly displacing any atoms which make up the permanent zeolite crystal structure. Zeolites can be used as catalysts for hydrocarbon conversion reactions, which can take place on outside surfaces of the zeolite as well as on internal surfaces within the pores of the zeolite.

In 1982, Wilson et al. developed aluminophosphate molecular sieves, the so-called AlPOs, which are microporous materials that have many of the same properties of zeolites, but are silica free, composed of $AlO_2^-$ and $PO_2^+$ tetrahedra, see U.S. Pat. No. 4,310,440. Subsequently, charge was introduced to the neutral aluminophosphate frameworks via the substitution of $SiO_2$ tetrahedra for $PO_2^+$ tetrahedra to produce the SAPO molecular sieves, see U.S. Pat. No. 4,440,871. Another way to introduce framework charge to neutral aluminophosphates is to substitute $[M^{2+}O_2]^{2-}$ tetrahedra for $AlO_2^-$ tetrahedra, which yield the MeAPO molecular sieves, see U.S. Pat. No. 4,567,029. It is furthermore possible to introduce framework charge on AlPO-based molecular sieves via the introduction both of $SiO_2$ and $[M^{2+}O_2]^{2-}$ tetrahedra to the framework, giving MeAPSO molecular sieves, see U.S. Pat. No. 4,973,785.

In these ground-breaking patents, metallophosphate materials with the LEV topology are disclosed. MAPO-35, a magnesium aluminophosphate material with the LEV topology is disclosed in U.S. Pat. No. 4,567,029 in which quinuclidine is employed as a structure directing agent. Likewise, U.S. Pat. No. 4,440,871 discloses SAPO-35, a silicoaluminophosphate that is also synthesized using the quinuclidine structure directing agent. In U.S. Pat. No. 4,973,785, the MeAPSO composition CoAPSO-35 is disclosed, which contains both cobalt and silicon in the framework in addition to Al and P and uses methylquinuclidine as the structure directing agent. After this early work, SAPO-35 was prepared using cyclohexylamine as a structure directing agent, see Lohse et. al, Crystal Research and Technology (1993), 28(8), 1101-1107. Subsequently, SAPO-35 has been prepared using hexamethyleneimine as a structure directing agent under a variety of conditions, including in ethylene glycol, see Venkatathri et. al., JCS Faraday Transactions (1997), 93(18), 3411-3415) and in aqueous and fluoride media, see Prakash et al, Chem. Mater. (1998), 10, 932-941. Wang et. al. have recently disclosed MAPO-35 materials containing Mg and synthesize using the N-methylpiperidine and 1,2-diaminocyclohexane as structure directing agents, see Dalton Transactions (2012), 41(22), 6855-6860). Most recently Cao et. al. have disclosed the preparation of SAPO-35 with the triethylmethylammonium structure directing agent, see US Pat. Appl. Publ. (2012), US 20120157741 A1.

In contrast to the above prior art, applicants have synthesized a variety of new materials and new structures using the very simple and commercially available ethyltrimethylammonium ($ETMA^+$) and diethyldimethylammonium ($DEDMA^+$) structure directing agents. One outcome of this investigation presented here is a new family of charged metallophosphate framework materials that contain a +3 valence metal, such as aluminum or gallium, and additionally at least one of a +2 valence metal, such as magnesium or zinc) and silicon, designated AlPO-67. When the +3 valence metal is Al, this corresponds to SAPO, MeAPO, and MeAPSO compositions. The AlPO-67 materials have the LEV topology that falls in the class of structures known as ABC-6 nets, see American Mineralogist, 66, 777-788 (1981). The microporous AlPO-67 materials can be prepared with the simple ethyltrimethylammonium ($ETMA^+$) and diethyldimethylammonium ($DEDMA^+$) structure directing agents.

SUMMARY OF THE INVENTION

As stated, the present invention relates to a new family of metallophosphate molecular sieves designated AlPO-67. Accordingly, one embodiment of the invention is a microporous crystalline material having a three-dimensional framework of at least $EO_2^-$ and $PO_2$ tetrahedral units and furthermore, at least one of $[M^{2+}O_2]^{2-}$ and $SiO_2$ tetrahedral units and an empirical composition in the as synthesized and anhydrous basis expressed by an empirical formula of:

$$R^+_r M^{2+}_m EP_x Si_y O_z$$

where M is at least one metal cation of valence +2 selected from the group consisting of $Be^{2+}$, $Mg^{2+}$, $Zn^{2+}$, $Co^{2+}$, $Mn^{2+}$, $Fe^{2+}$, $Ni^{2+}$, "m" is the mole ratio of M to E and varies from 0 to about 1.0, R is an organoammonium cation selected from the group consisting of ethyltrimethylammonium ($ETMA^+$), diethyldimethylammonium ($DEDMA^+$) and mixtures thereof, "r" is the mole ratio of R to E and has a value of about 0.1 to about 2.0, E is an +3 valence element selected from the group consisting of aluminum, gallium, iron, boron and mixtures thereof, "x" is mole ratio of P to E and varies from 0.5 to about 2.0, "y" is the mole ratio of Si to E and varies from 0 to about 1.0, "m"+"y"≥0.02, and "z" is the mole ratio of O to E and has a value determined by the equation:

$$z=(2 \cdot m + r + 3 + 5 \cdot x + 4 \cdot y)/2$$

and is characterized in that it has the x-ray diffraction pattern having at least the d-spacings and intensities set forth in Table A1:

TABLE A1

| 2Θ | d(Å) | I/I₀% |
|---|---|---|
| 8.86-8.39 | 9.97-10.53 | w-m |
| 11.21-10.51 | 7.89-8.41 | m-s |
| 13.65-13.16 | 6.48-6.72 | m-vs |
| 17.72-16.91 | 5.00-5.24 | m-vs |
| 21.29-20.69 | 4.17-4.29 | m-s |
| 22.43-21.5 | 3.96-4.13 | s-vs |
| 23.84-22.84 | 3.73-3.89 | w-vs |
| 27.51-26.51 | 3.24-3.36 | w-m |
| 29.06-27.95 | 3.07-3.19 | w-m |
| 32.90-31.59 | 2.72-2.83 | m |
| 35.02-33.93 | 2.56-2.64 | w-m |
| 36.65-35.31 | 2.45-2.54 | w-m |
| 52.23-50.67 | 1.75-1.80 | w-m | and in another embodiment may be characterized by an x-ray pattern having at least the d-spacings and intensities set forth in Table A2:

TABLE A2

| 2Θ | d(Å) | I/I₀% |
|---|---|---|
| 8.86-8.39 | 9.97-10.53 | w-m |
| 11.21-10.51 | 7.89-8.41 | m-s |
| 11.90-11.44 | 7.43-7.73 | w |
| 13.65-13.16 | 6.48-6.72 | m-vs |
| 16.31-15.64 | 5.43-5.66 | w-m |
| 17.72-16.91 | 5.00-5.24 | m-vs |
| 18.09-17.51 | 4.90-5.06 | w-m |
| 21.29-20.69 | 4.17-4.29 | m-s |
| 22.43-21.50 | 3.96-4.13 | s-vs |
| 23.84-22.84 | 3.73-3.89 | w-vs |
| 25.43-24.57 | 3.50-3.62 | w |
| 27.51-26.51 | 3.24-3.36 | w-m |
| 29.06-27.95 | 3.07-3.19 | w-m |
| 29.76-28.59 | 3.00-3.12 | w-m |
| 32.90-31.59 | 2.72-2.83 | m |
| 35.02-33.93 | 2.56-2.64 | w-m |
| 36.65-35.31 | 2.45-2.54 | w-m |
| 42.40-41.38 | 2.13-2.18 | w |
| 49.21-47.83 | 1.85-1.90 | w |
| 52.23-50.67 | 1.75-1.80 | w-m |

Another embodiment of the invention is a process for preparing the crystalline microporous metallophosphate molecular sieve described above. The process comprises forming a reaction mixture containing reactive sources of R, E, P, one or both of M and Si, and heating the reaction mixture at a temperature of about 60° C. to about 200° C. for a time sufficient to form the molecular sieve, the reaction mixture having a composition expressed in terms of mole ratios of the oxides of:

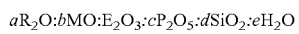

where "a" has a value of about 0.25 to about 16, "b" has a value of about 0 to about 2, "c" has a value of about 0.8 to about 8, "d" has a value of about 0 to about 4, and "e" has a value from 30 to 800, and wherein the sum of the values of "b" and "d" is greater than 0.01.

Yet another embodiment of the invention is a hydrocarbon conversion process using the above-described molecular sieve as a catalyst. The process comprises contacting at least one hydrocarbon with the molecular sieve at conversion conditions to generate at least one converted hydrocarbon.

Still another embodiment of the invention is a separation process using the crystalline AlPO-67 material. The process may involve separating mixtures of molecular species or removing contaminants by contacting a fluid with the AlPO-67 molecular sieve. Separation of molecular species can be based either on the molecular size (kinetic diameter) or on the degree of polarity of the molecular species. Removing contaminants may be by ion exchange with the molecular sieve.

DETAILED DESCRIPTION OF THE INVENTION

Applicants have prepared a family of metallophosphate materials with the ETMA$^+$ and DEDMA$^+$ structure directing agents whose topological structure is LEV, see http://izasc-mirror.la.asu.edu/fmi/xsl/IZA-SC/ftc_fw.xsl?-db=Atlas_main&-lay=fw&-max=25&STC=LEV&-find. In their paper "Enumeration of 4-connected 3-dimensional nets and classification of framework silicates: the infinite set of ABC-6 nets; the Archimedean and 6-related nets," Smith and Bennett state "To a first approximation, all silicates belonging to the ABC-6 net family have x-ray diffraction patterns which can be indexed on a hexagonal prismatic unit cell with lattice parameters a~13.0±0.3 Å and c~p×(2.6±0.1 Å).", see American Mineralogist, 66, 777-788 (1981). The AlPO-67 materials index on such hexagonal unit cells as one SAPO-67 material has lattice parameters a=13.155 Å and c=22.813 Å, which is suggests an ABC-6 net structure with the stacking sequence repeating every 9 layers along the c-axis (p=22.813/2.5=9.12), a characteristic of the LEV topology. AlPO-67 is the fourth ABC 6-net topology isolated in our investigation of the structure directing properties of ETMA$^+$ and DEDMA$^+$. The instant microporous crystalline material (AlPO-67) has an empirical composition in the as-synthesized form and on an anhydrous basis expressed by the empirical formula:

$$R^+_r M^{2+}_m EP_x Si_y O_z$$

where M is at least one divalent cation and is selected from the group consisting of alkaline earth and transition metals. Specific examples of the M cations include but are not limited to beryllium, magnesium, cobalt (II), manganese, zinc, iron(II), nickel and mixtures thereof. R is an organoammonium cation, examples of which include but are not limited to ethyltrimethylammonium (ETMA$^+$), and diethyldimethylammonium (DEDMA$^+$) and mixtures thereof and "r" is the mole ratio of R to E and varies from about 0.1 to about 2.0. The value of "m" is the mole ratio of M to E and varies from 0 to about 1.0, "x" is mole ratio of P to E and varies from 0.5 to about 2.0. The ratio of silicon to E is represented by "y" which varies from about 0 to about 1.0 and "m"+"y"≥0.02. E is an trivalent element which is tetrahedrally coordinated, is present in the framework and is selected from the group consisting of aluminum, gallium, iron(III) and boron. Lastly, "z" is the mole ratio of O to E and is given by the equation:

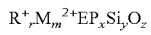

The microporous crystalline metallophosphate AlPO-67 is prepared by a hydrothermal crystallization of a reaction mixture prepared by combining reactive sources of R, E, phosphorous, and one or both of M and silicon. A preferred form of the AlPO-67 materials is when E is Al. The sources of aluminum include but are not limited to aluminum alkoxides, precipitated aluminas, aluminum metal, aluminum hydroxide, aluminum salts and alumina sols. Specific examples of aluminum alkoxides include, but are not limited to aluminum ortho sec-butoxide and aluminum ortho isopropoxide. Sources of the other E elements include but are not limited to organoammonium borates, boric acid, precipitated gallium oxyhydroxide, gallium sulfate, ferric sulfate, and ferric chloride. Sources of phosphorus include, but are not limited to, orthophosphoric acid, phosphorus pentoxide, and ammonium dihydrogen phosphate. Sources of silica include but are not limited to tetraethylorthosilicate, colloidal silica, and precipitated silica. Sources of the M metals include the halide salts, nitrate salts, acetate salts, and sulfate salts of the respective alkaline earth and transition metals. R is an organoammonium cation selected from the group consisting of ETMA⁺ and DEDMA⁺, and mixtures thereof, and the sources include the hydroxide, chloride, bromide, iodide and fluoride compounds. Specific examples include without limitation ethyltrimethylammonium hydroxide, ethyltrimethylammonium chloride, diethyldimethylammonium chloride and diethyldimethylammonium hydroxide. In one embodiment R is ETMA⁺. In another embodiment R is DEDMA⁺. In yet another embodiment, R is a combination of ETMA⁺ and DEDMA⁺.

The reaction mixture containing reactive sources of the desired components can be described in terms of molar ratios of the oxides by the formula:

$$aR_2O:bMO:E_2O_3:cP_2O_5:dSiO_2:eH_2O$$

where "a" varies from about 0.25 to about 16, "b" varies from about 0 to about 2, "c" varies from about 0.8 to about 8, "d" varies from about 0 to about 4, and "e" varies from 30 to about 800, and wherein the sum of the values of "b" and "d" is greater than 0.01. If alkoxides are used, a distillation or evaporative step may be included to remove the alcohol hydrolysis products. The reaction mixture is now reacted at a temperature of about 60° C. to about 200° C., or in another embodiment from about 125° C. to about 175° C., for a period of about 1 day to about 3 weeks, or in another embodiment for about 2 days to about 10 days, in a sealed reaction vessel at autogenous pressure. After crystallization is complete, the solid product is isolated from the heterogeneous mixture by means such as filtration or centrifugation, and then washed with deionized water and dried in air at ambient temperature up to about 100° C. AlPO-67 seeds can optionally be added to the reaction mixture in order to accelerate the formation of the desired microporous composition.

The AlPO-67 metallophosphate-based material, which is obtained from the above-described process, is characterized by the x-ray diffraction pattern, having at least the d-spacings and relative intensities set forth in Table A1 below.

TABLE A1

| 2Θ | d(Å) | I/I₀ % |
|---|---|---|
| 8.86-8.39 | 9.97-10.53 | w-m |
| 11.21-10.51 | 7.89-8.41 | m-s |
| 13.65-13.16 | 6.48-6.72 | m-vs |
| 17.72-16.91 | 5.00-5.24 | m-vs |
| 21.29-20.69 | 4.17-4.29 | m-s |
| 22.43-21.5 | 3.96-4.13 | s-vs |
| 23.84-22.84 | 3.73-3.89 | w-vs |
| 27.51-26.51 | 3.24-3.36 | w-m |
| 29.06-27.95 | 3.07-3.19 | w-m |
| 32.90-31.59 | 2.72-2.83 | m |
| 35.02-33.93 | 2.56-2.64 | w-m |
| 36.65-35.31 | 2.45-2.54 | w-m |
| 52.23-50.67 | 1.75-1.80 | w-m |

In another embodiment of the invention, AlPO-67 metallophosphate, which is obtained from the above-described process, is characterized by the x-ray diffraction pattern, having at least the d-spacings and relative intensities set forth in Table A2 below.

TABLE A2

| 2Θ | d(Å) | I/I₀ % |
|---|---|---|
| 8.86-8.39 | 9.97-10.53 | w-m |
| 11.21-10.51 | 7.89-8.41 | m-s |

TABLE A2-continued

| 2Θ | d(Å) | I/I₀ % |
|---|---|---|
| 11.90-11.44 | 7.43-7.73 | w |
| 13.65-13.16 | 6.48-6.72 | m-vs |
| 16.31-15.64 | 5.43-5.66 | w-m |
| 17.72-16.91 | 5.00-5.24 | m-vs |
| 18.09-17.51 | 4.90-5.06 | w-m |
| 21.29-20.69 | 4.17-4.29 | m-s |
| 22.43-21.50 | 3.96-4.13 | s-vs |
| 23.84-22.84 | 3.73-3.89 | w-vs |
| 25.43-24.57 | 3.50-3.62 | w |
| 27.51-26.51 | 3.24-3.36 | w-m |
| 29.06-27.95 | 3.07-3.19 | w-m |
| 29.76-28.59 | 3.00-3.12 | w-m |
| 32.90-31.59 | 2.72-2.83 | m |
| 35.02-33.93 | 2.56-2.64 | w-m |
| 36.65-35.31 | 2.45-2.54 | w-m |
| 42.40-41.38 | 2.13-2.18 | w |
| 49.21-47.83 | 1.85-1.90 | w |
| 52.23-50.67 | 1.75-1.80 | w-m |

In one embodiment of the invention, the AlPO-67 is thermally stable up to a temperature of at least 400° C., and in another embodiment the AlPO-67 is thermally stable up to a temperature of at least 500° C.

The AlPO-67 may be modified in many ways to tailor it for use in a particular application. Modifications include calcination, ammonia calcinations, ion-exchange, steaming, various acid extractions, ammonium hexafluorosilicate treatment, or any combination thereof, as outlined for the case of UZM-4 in U.S. Pat. No. 6,776,975 B1 which is incorporated by reference in its entirety. Properties that may be modified include porosity, adsorption, framework composition, acidity, thermal stability, etc.

As synthesized, the AlPO-67 material will contain some of the exchangeable or charge balancing cations in its pores. These exchangeable cations can be exchanged for other cations, or in the case of organic cations, they can be removed by heating under controlled conditions. A preferred method of removing organic cations from the pores is ammonia calcination. Calcination in air converts the organic cations in the pores to protons, which can, for example, lead to some removal of Al from the framework upon exposure to water vapor. When the calcination is carried out in an ammonia atmosphere, the organic cation in the pore is replaced by NH₄⁺ cation and the framework remains intact, see Studies in Surface Science, (2004) vol. 154, p. 1324-1331. Typical conditions for ammonia calcinations include the use of gaseous anhydrous ammonia flowing at a rate of 1.1 l/min while ramping the sample at 2-5° C./min to 500° C. and holding at that temperature for a time ranging from 5 minutes to 5 hours. The resulting ammonium form of AlPO-67 has essentially the diffraction pattern of Table A1. The ammonium form of AlPO-67 may then be ion-exchanged to any other form, resulting in a material with a modified composition, AlPO-67M, given by the empirical formula:

$$M'^{p+}_n M^{2+}_m EP_x Si_y O_z$$

where M is at least one framework metal cation of valence +2 selected from the group consisting of Be²⁺, Mg²⁺, Zn²⁺, Co²⁺, Mn²⁺, Fe²⁺, Ni²⁺, "m" is the mole ratio of M to E and varies from 0 to about 1.0, M' is selected from the group consisting if NH₄⁺, H⁺, alkali metals, alkaline earth metals, rare earth metals and mixtures thereof, "n" is the mole ratio of M' to E and has a value of about 0.03 to about 2.0, "p" is the weighted average valence of M' and varies from 1 to about 3, E is a trivalent element selected from the group consisting of aluminum, gallium, iron, boron and mixtures thereof, "x" is mole ratio of P to E and varies from 0.5 to about 2.0, "y" is the mole ratio of Si to E and varies from 0 to about 1.0, "m"+"y"≥0.02, and "z" is the mole ratio of O to E and has a value determined by the equation:

$$z=(p \cdot n+2 \cdot m+3+5 \cdot x+4 \cdot y)/2$$

and is characterized in that it has the x-ray diffraction pattern having at least the d-spacings and intensities set forth in Table A1:

TABLE A1

| 2Θ | d(Å) | I/I$_0$ % |
|---|---|---|
| 8.86-8.39 | 9.97-10.53 | w-m |
| 11.21-10.51 | 7.89-8.41 | m-s |
| 13.65-13.16 | 6.48-6.72 | m-vs |
| 17.72-16.91 | 5.00-5.24 | m-vs |
| 21.29-20.69 | 4.17-4.29 | m-s |
| 22.43-21.5 | 3.96-4.13 | s-vs |
| 23.84-22.84 | 3.73-3.89 | w-vs |
| 27.51-26.51 | 3.24-3.36 | w-m |
| 29.06-27.95 | 3.07-3.19 | w-m |
| 32.90-31.59 | 2.72-2.83 | m |
| 35.02-33.93 | 2.56-2.64 | w-m |
| 36.65-35.31 | 2.45-2.54 | w-m |
| 52.23-50.67 | 1.75-1.80 | w-m |

When AlPO-67 is calcined in air, there can be loss of metal from the framework, such as Al, which can alter the x-ray diffraction pattern from that observed for the as-synthesized AlPO-67, see Studies in Surface Science, (2004) vol. 154, p. 1324-1331. Some AlPO-67 compositions may not be stable to air calcination and subsequent exposure to water. The stable air calcined AlPO-67 materials, AlPO-67C, are characterized on an anhydrous basis by the empirical formula:

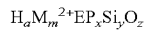

$$H_a M_m^{2+} E P_x Si_y O_z$$

where M is at least one metal cation of valence +2 selected from the group consisting of $Be^{2+}$, $Mg^{2+}$, $Zn^{2+}$, $Co^{2+}$, $Mn^{2+}$, $Fe^{2+}$, $Ni^{2+}$, "m" is the mole ratio of M to E and varies from 0 to about 1.0, H is a proton, "a" is the mole ratio of H to E and has a value of about 0.1 to about 2.0, E is an trivalent element selected from the group consisting of aluminum, gallium, iron, boron and mixtures thereof, "x" is mole ratio of P to E and varies from 0.5 to about 2.0, "y" is the mole ratio of Si to E and varies from 0.0 to about 1.0, "m"+"y"≥0.02, and "z" is the mole ratio of 0 to E and has a value determined by the equation:

$$z=(a+2 \cdot m+3+5 \cdot x+4 \cdot y)/2$$

and is characterized in that it has the x-ray diffraction pattern having at least the d-spacings and intensities set forth in Table B:

TABLE B

| 2Θ | d(Å) | I/I$_0$ % |
|---|---|---|
| 9.02-8.33 | 9.80-10.6 | w-m |
| 11.09-10.79 | 7.97-8.19 | vs |
| 13.74-13.32 | 6.44-6.64 | s-vs |
| 17.58-16.97 | 5.04-5.22 | m |
| 21.19-20.69 | 4.19-4.29 | m |
| 22.32-21.87 | 3.98-4.06 | m-s |
| 28.78-28.13 | 3.10-3.17 | m |
| 32.78-32.05 | 2.73-2.79 | w-m |

The crystalline AlPO-67 materials of this invention can be used for separating mixtures of molecular species, removing contaminants through ion exchange and catalyzing various hydrocarbon conversion processes. Separation of molecular species can be based either on the molecular size (kinetic diameter) or on the degree of polarity of the molecular species. The separation involves contacting the mixture to be separated with the AlPO-67 material. Further processing may be involved.

The AlPO-67 compositions of this invention can also be used as a catalyst or catalyst support in various hydrocarbon conversion processes. Hydrocarbon conversion processes are well known in the art and include cracking, hydrocracking, alkylation of both aromatics and isoparaffin, isomerization, polymerization, reforming, hydrogenation, dehydrogenation, transalkylation, dealkylation, hydration, dehydration, hydrotreating, hydrodenitrogenation, hydrodesulfurization, methanol to olefins, methanation and syngas shift process. Specific reaction conditions and the types of feeds which can be used in these processes are set forth in U.S. Pat. No. 4,310,440, U.S. Pat. No. 4,440,871 and U.S. Pat. No. 5,126,308, which are incorporated by reference. Preferred hydrocarbon conversion processes are those in which hydrogen is a component such as hydrotreating or hydrofining, hydrogenation, hydrocracking, hydrodenitrogenation, hydrodesulfurization, etc.

Hydrocracking conditions typically include a temperature in the range of 400° to 1200° F. (204-649° C.), preferably between 600° and 950° F. (316-510° C.). Reaction pressures are in the range of atmospheric to about 3,500 psig (24,132 kPa g), preferably between 200 and 3000 psig (1379-20,685 kPa g). Contact times usually correspond to liquid hourly space velocities (LHSV) in the range of about 0.1 hr$^{-1}$ to 15 hr$^{-1}$, preferably between about 0.2 and 3 hr$^{-1}$. Hydrogen circulation rates are in the range of 1,000 to 50,000 standard cubic feet (scf) per barrel of charge (178-8,888 std. m$^3$/m$^3$), preferably between 2,000 and 30,000 scf per barrel of charge (355-5,333 std. m$^3$/m$^3$). Suitable hydrotreating conditions are generally within the broad ranges of hydrocracking conditions set out above.

The reaction zone effluent is normally removed from the catalyst bed, subjected to partial condensation and vapor-liquid separation and then fractionated to recover the various components thereof. The hydrogen, and if desired some or all of the unconverted heavier materials, are recycled to the reactor. Alternatively, a two-stage flow may be employed with the unconverted material being passed into a second reactor. Catalysts of the subject invention may be used in just one stage of such a process or may be used in both reactor stages.

Catalytic cracking processes are preferably carried out with the AlPO-67 composition using feedstocks such as gas oils, heavy naphthas, deasphalted crude oil residua, etc. with gasoline being the principal desired product. Temperature conditions of 850° to 1100° F., LHSV values of 0.5 to 10 and pressure conditions of from about 0 to 50 psig are suitable.

Alkylation of aromatics usually involves reacting an aromatic ($C_2$ to $C_{12}$), especially benzene, with a monoolefin to produce a linear alkyl substituted aromatic. The process is carried out at an aromatic:olefin (e.g., benzene:olefin) ratio of between 5:1 and 30:1, a LHSV of about 0.3 to about 6 hr$^{-1}$, a temperature of about 100° to about 250° C. and pressures of about 200 to about 1000 psig. Further details on apparatus may be found in U.S. Pat. No. 4,870,222 which is incorporated by reference.

Alkylation of isoparaffins with olefins to produce alkylates suitable as motor fuel components is carried out at temperatures of −30° to 40° C., pressures from about atmospheric to about 6,894 kPa (1,000 psig) and a weight hourly space velocity (WHSV) of 0.1 to about 120. Details on paraffin alkylation may be found in U.S. Pat. No. 5,157,196 and U.S. Pat. No. 5,157,197, which are incorporated by reference The conversion of methanol to olefins is effected by contacting the methanol with the AlPO-67 catalyst at conversion conditions, thereby forming the desired olefins. The methanol can be in the liquid or vapor phase with the vapor phase being preferred. Contacting the methanol with the AlPO-67 catalyst can be done in a continuous mode or a batch mode with a continuous mode being preferred. The amount of time that the methanol is in contact with the AlPO-67 catalyst must be sufficient to convert the methanol to the desired light olefin products. When the process is carried out in a batch process, the contact time varies from about 0.001 hrs to about 1 hr and preferably from about 0.01 hr to about 1.0 hr. The longer contact times are used at lower temperatures while shorter times are used at higher temperatures. Further, when the process is carried out in a continuous mode, the Weight Hourly Space Velocity (WHSV) based on methanol can vary from about 1 $hr^{-1}$ to about 1000 $hr^{-1}$ and preferably from about 1 $hr^{-1}$ to about 100 $hr^{-1}$.

Generally, the process must be carried out at elevated temperatures in order to form light olefins at a fast enough rate. Thus, the process should be carried out at a temperature of about 300° C. to about 600° C., preferably from about 400° C. to about 550° C. and most preferably from about 450° C. to about 525° C. The process may be carried out over a wide range of pressure including autogenous pressure. Thus, the pressure can vary from about 0 kPa (0 psig) to about 1724 kPa (250 psig) and preferably from about 34 kPa (5 psig) to about 345 kPa (50 psig).

Optionally, the methanol feedstock may be diluted with an inert diluent in order to more efficiently convert the methanol to olefins. Examples of the diluents which may be used are helium, argon, nitrogen, carbon monoxide, carbon dioxide, hydrogen, steam, paraffinic hydrocarbons, e.g., methane, aromatic hydrocarbons, e.g., benzene, toluene and mixtures thereof. The amount of diluent used can vary considerably and is usually from about 5 to about 90 mole percent of the feedstock and preferably from about 25 to about 75 mole percent.

The actual configuration of the reaction zone may be any well known catalyst reaction apparatus known in the art. Thus, a single reaction zone or a number of zones arranged in series or parallel may be used. In such reaction zones the methanol feedstock is flowed through a bed containing the AlPO-67 catalyst. When multiple reaction zones are used, one or more AlPO-67 catalysts may be used in series to produce the desired product mixture. Instead of a fixed bed, a dynamic bed system, e.g., fluidized or moving, may be used. Such a dynamic system would facilitate any regeneration of the AlPO-67 catalyst that may be required. If regeneration is required, the AlPO-67 catalyst can be continuously introduced as a moving bed to a regeneration zone where it can be regenerated by means such as oxidation in an oxygen containing atmosphere to remove carbonaceous materials.

The following examples are presented in illustration of this invention and are not intended as undue limitations on the generally broad scope of the invention as set out in the appended claims. The products will be designated with names that contain the suffix "-67" to indicate the "-67" structure and prefix that reflects the compositional nature of the product, such as "SAPO" for a silicoaluminophosphate, MAPO for a metalloaluminophosphasate, and MAPSO for a silicometalloaluminophosphate, etc.

The structure of the AlPO-67 compositions of this invention was determined by x-ray analysis. The x-ray patterns presented in the following examples were obtained using standard x-ray powder diffraction techniques. The radiation source was a high-intensity, x-ray tube operated at 45 kV and 35 mA. The diffraction pattern from the copper K-alpha radiation was obtained by appropriate computer based techniques. Flat compressed powder samples were continuously scanned at 2° to 56° (2θ). Interplanar spacings (d) in Angstrom units were obtained from the position of the diffraction peaks expressed as θ where θ is the Bragg angle as observed from digitized data. Intensities were determined from the integrated area of diffraction peaks after subtracting background, "$I_o$" being the intensity of the strongest line or peak, and "I" being the intensity of each of the other peaks.

As will be understood by those skilled in the art the determination of the parameter 2θ is subject to both human and mechanical error, which in combination can impose an uncertainty of about ±0.4° on each reported value of 2θ. This uncertainty is, of course, also manifested in the reported values of the d-spacings, which are calculated from the 2θ values. This imprecision is general throughout the art and is not sufficient to preclude the differentiation of the present crystalline materials from each other and from the compositions of the prior art. In some of the x-ray patterns reported, the relative intensities of the d-spacings are indicated by the notations vs, s, m, and w which represent very strong, strong, medium, and weak, respectively. In terms of 100×I/$I_o$, the above designations are defined as:

$$w=0-15; \ m=15-60; \ s=60-80 \text{ and } vs=80-100$$

In certain instances the purity of a synthesized product may be assessed with reference to its x-ray powder diffraction pattern. Thus, for example, if a sample is stated to be pure, it is intended only that the x-ray pattern of the sample is free of lines attributable to crystalline impurities, not that there are no amorphous materials present.

In order to more fully illustrate the invention, the following examples are set forth. It is to be understood that the examples are only by way of illustration and are not intended as an undue limitation on the broad scope of the invention as set forth in the appended claims.

EXAMPLE 1

A Teflon beaker was charged with 15.15 g $H_3PO_4$ (85%) to which 13.23 g deionized water was added with stirring. Separately, 5.00 g Zn(OAc)$_2$*2H$_2$O was dissolved in 50.00 g deionized water. This solution was added to the $H_3PO_4$ with vigorous stirring. Next, 11.1 g Al(OH)$_3$ (80.0%) was added slowly and intermittently to allow the formation of a milky suspension. After the addition was completed, the reaction mixture was homogenized for 2 hours. Over a period of about 3 minutes, 40.75 g DEDMAOH (20%) was added in 5 pours. The mixture was stirred for 20 minutes. Portions of the reaction mixture were distributed among 7 Teflon-lined autoclaves and digested at autogenous pressure at range of temperatures for different time periods. The products were isolated by centrifugation and washed with de-ionized water, and dried at room temperature. The products from the 100° C. and 125° C. reactions that were digested for 36 hours were identified as MAPO-67 via powder x-ray diffraction. The diffraction lines representative of the 125° C. product are shown below in Table 1.

TABLE 1

| 2-Θ | d(Å) | I/$I_0$ % |
| --- | --- | --- |
| 8.70 | 10.16 | m |
| 11.00 | 8.04 | s |
| 11.78 | 7.50 | w |

TABLE 1-continued

| 2-Θ | d(Å) | I/I₀ % |
|---|---|---|
| 13.38 | 6.61 | m |
| 15.98 | 5.54 | w |
| 17.38 | 5.10 | s |
| 17.88 | 4.96 | w |
| 21.10 | 4.21 | m |
| 21.94 | 4.05 | vs |
| 23.28 | 3.82 | m |
| 25.16 | 3.54 | w |
| 26.90 | 3.31 | m |
| 28.56 | 3.12 | m |
| 29.39 | 3.04 | w |
| 32.12 | 2.78 | m |
| 34.48 | 2.60 | w |
| 35.82 | 2.50 | w |
| 42.02 | 2.15 | w |
| 42.40 | 2.13 | w |
| 42.78 | 2.11 | w |
| 44.62 | 2.03 | w |
| 48.54 | 1.87 | w |
| 51.32 | 1.78 | w |

EXAMPLE 2

A Teflon beaker was charged with 97.76 g DEDMAOH (20%) and placed under a high speed mixer. To this solution, 4.60 g Al(OH)₃ (26.7%) was added in three portions and this dissolved to form a clear solution. Next, 13.12 g H₃PO₄ (85%) was added dropwise, resulting in a clear solution. Separately, 2.23 g Mn(OAc)₂*4H₂O was dissolved in 10.00 g de-ionized water. This solution was added dropwise and immediately introduced some haziness to reaction mixture, so the addition was terminated. Then 1.01 g H₃PO₄ (85%) was diluted with 1.00 g de-ionized water and added to the reaction mixture in a single pour. The reaction mixture was stirred until it was clear. Then the addition of the Mn acetate solution was continued. The reaction mixture was homogenized for an additional 30 minutes after completion of the addition, at which time it was a clear solution. The reaction mixture was distributed among several Teflon-lined autoclaves and digested at autogenous pressure at a variety of temperatures and time periods. The products were isolated by centrifugation, washed with de-ionized water and dried at room temperature. The portion of the reaction mixture digested at 175° C. for 36 hours yielded MAPO-67, which was identified by powder x-ray diffraction. Representative lines in the diffraction pattern for the MAPO-67 product are given in Table 2.

TABLE 2

| 2-Θ | d(Å) | I/I₀ % |
|---|---|---|
| 8.58 | 10.30 | w |
| 10.86 | 8.14 | m |
| 11.58 | 7.64 | w |
| 13.28 | 6.66 | m |
| 15.81 | 5.60 | w |
| 17.20 | 5.15 | s |
| 17.66 | 5.02 | w |
| 20.82 | 4.26 | m |
| 21.80 | 4.07 | vs |
| 23.12 | 3.84 | m |
| 24.80 | 3.59 | w |
| 26.76 | 3.33 | m |
| 28.24 | 3.16 | m |
| 28.96 | 3.08 | w |
| 31.40 | 2.85 | w |
| 32.02 | 2.79 | m |
| 34.24 | 2.62 | w |

TABLE 2-continued

| 2-Θ | d(Å) | I/I₀ % |
|---|---|---|
| 34.81 | 2.58 | w |
| 35.22 | 2.55 | w |
| 35.68 | 2.51 | w |
| 36.80 | 2.44 | w |
| 41.74 | 2.16 | w |
| 44.52 | 2.03 | w |
| 47.56 | 1.91 | w |
| 48.21 | 1.89 | w |
| 49.40 | 1.84 | w |
| 50.96 | 1.79 | w |
| 54.87 | 1.67 | w |
| 55.16 | 1.66 | w |

EXAMPLE 3

A Teflon beaker was charged with 100.00 g DEDMAOH (20%) which was placed under a high speed stirrer. Then 4.65 g Al(OH)₃ (78.1%) was added intermittently with stirring until it was all nearly dissolved. Phosphoric acid (85%), 19.34 g, was continuously added dropwise until the addition was completed, during which time the reaction mixture became a clear solution. Separately, 2.05 g Zn(OAc)₂*2H₂O was dissolved in 10.00 g de-ionized water. This solution was added dropwise to the reaction mixture, which was hazy but cleared up with homogenization. The reaction mixture was distributed among 7 Teflon-lined autoclaves and digested at autogenous pressure at a variety of temperatures and time periods. The products were isolated by centrifugation, washed with de-ionized water, and dried at room temperature. Over the entire range of conditions examined, 95° C. to 175° C. for 61-159 hours, the reactions yielded MAPO-67 as the product, which were identified by powder x-ray diffraction. The characteristic diffraction lines for the 150° C./61 hour product are given below in Table 3. Elemental analysis on this same product shows the composition to consist of the elemental ratios N/Al=0.25, Zn/Al=0.26, and P/Al=1.22, while C/N=6.32. A portion of this material was calcined at 500° C., using a ramp rate of 2° C./min in a nitrogen atmosphere, calcining in nitrogen for 4 hours before switching to dry air and calcining for an additional 2 hours at 500° C. The material was identified as AlPO-67C by powder x-ray diffraction. The diffraction lines for the calcined material are shown in table 3 below.

TABLE 3

| Example 3 | | | Example 3 calcined | | |
|---|---|---|---|---|---|
| 2-Θ | d(Å) | I/I₀ % | 2Θ | d(Å) | I/I₀ % |
| 8.50 | 10.39 | w | 8.49 | 10.41 | w |
| 10.68 | 8.28 | m | 10.88 | 8.13 | vs |
| 13.28 | 6.66 | m | 13.62 | 6.50 | vs |
| 17.10 | 5.18 | m | 17.14 | 5.17 | m |
| 20.85 | 4.26 | m | 20.96 | 4.23 | m |
| 20.90 | 4.25 | m | 21.5 | 4.13 | m |
| 21.72 | 4.09 | vs | 22.14 | 4.01 | m |
| 23.10 | 3.85 | m | 28.34 | 3.15 | m |
| 26.82 | 3.32 | m | 32.54 | 2.75 | m |
| 28.70 | 3.11 | m | | | |
| 31.98 | 2.80 | m | | | |
| 32.69 | 2.74 | w | | | |
| 34.56 | 2.59 | w | | | |
| 35.60 | 2.52 | w | | | |
| 42.01 | 2.15 | w | | | |
| 42.21 | 2.14 | w | | | |
| 48.68 | 1.87 | w | | | |
| 51.16 | 1.78 | w | | | |
| 55.13 | 1.66 | w | | | |

EXAMPLE 4

A Teflon beaker was charged with 130.00 g ETMAOH (20%) and placed under a high speed stirrer. Then 3.71 g LUDOX AS-40™ colloidal silica (40% $SiO_2$) was added, stirred briefly and the reaction mixture was transferred to Teflon bottle, sealed, and placed in an oven at 100° C. for one hour. The resulting solution was returned to the Teflon beaker and 12.34 g $Al(OH)_3$ (78.1%) was added with vigorous stirring, stirring for an hour after the addition was completed. Then 35.62 g $H_3PO_4$ (85%) was added dropwise and intermittently. At the end of the addition, the solution was nearly clear. After homogenizing for another hour, the reaction mixture was distributed among 8 teflon-lined autoclaves and digested at autogenous pressure at a variety of temperatures and time periods. The products were isolated by centrifugation, washed with de-ionized water, and dried at room temperature. All of the products, digested under conditions ranging from 24-209 hours and 150-200° C., were identified as SAPO-67 via powder x-ray diffraction. Representative diffraction lines for the product from the 175° C./109 hour digestion are given below in Table 4. Elemental analysis on this product showed the composition to consist of the elemental ratios N/Al=0.17, Na/Al=0.02 (from Ludox AS-40™), Si/Al=0.22, P/Al=0.81, while C/N=5.21.

TABLE 4

| 2-Θ | d(Å) | $I/I_0$ % |
|---|---|---|
| 8.64 | 10.22 | w |
| 10.96 | 8.07 | m |
| 11.63 | 7.60 | w |
| 13.40 | 6.60 | m |
| 15.98 | 5.54 | w |
| 17.36 | 5.11 | s |
| 17.79 | 4.98 | w |
| 20.96 | 4.24 | m |
| 21.98 | 4.04 | vs |
| 23.32 | 3.81 | m |
| 24.96 | 3.56 | w |
| 27.00 | 3.30 | m |
| 28.44 | 3.14 | m |
| 29.22 | 3.05 | w |
| 31.60 | 2.83 | w |
| 32.24 | 2.77 | m |
| 34.42 | 2.60 | w |
| 35.11 | 2.55 | w |
| 35.96 | 2.50 | w |
| 37.79 | 2.38 | w |
| 41.03 | 2.20 | w |
| 41.98 | 2.15 | w |
| 42.76 | 2.11 | w |
| 44.79 | 2.02 | w |
| 47.82 | 1.90 | w |
| 48.58 | 1.87 | w |
| 49.00 | 1.86 | w |
| 49.74 | 1.83 | w |
| 51.32 | 1.78 | w |
| 55.20 | 1.66 | w |
| 55.60 | 1.65 | w |

EXAMPLE 5

A Teflon beaker was charged with 100.00 g ETMAOH (20%) and placed under a high speed mixer. Then 7.61 g Ludox AS-40™ colloidal silica (40% $SiO_2$) was added to the reaction mixture, which was stirred briefly, transferred to a Teflon bottle, sealed, and digested in an oven at 95° C. for 1 hour. The resulting solution was transferred back to the beaker, placed under the stirrer, and 25.31 g $Al(OH)_3$ (78.1%) was added in small portions. After initially dissolving, a white suspension eventually formed. The reaction mixture was homogenized for 20 minutes after the addition. Separately, 43.84 g $H_3PO_4$ (85%) was diluted with 22.83 g de-ionized water. This was added dropwise to the reaction mixture, intermittently, allowing the mixture to stir between additions. At a certain point during the addition the reaction mixture got very thick and some hand mixing was required before going to high speed mixing while supporting the beaker. The remainder of the phosphoric acid solution was added while mixing vigorously. The resulting reaction mixture was a moist homogenous viscous white gel. The reaction mixture was distributed among 8 Teflon-lined autoclaves and digested at autogenous pressure at a variety of temperatures and times. The products were isolated by centrifugation, washed with de-ionized water and dried at room temperature. X-ray diffraction analysis identified the products from 150 and 175° C. digestions as SAPO-67, while the 200° C. digestions started to show SAPO-67 with impurities after 2 days. Characteristic diffraction lines for the product resulting from 150° C./108 hour digestion are shown below in Table 5 A portion of this material was calcined at 500° C., using a ramp rate of 2° C./min in a nitrogen atmosphere, calcining in nitrogen for 4 hours before switching to dry air and calcining for an additional 2 hours at 500° C. The material was identified as AlPO-67C by powder x-ray diffraction. The diffraction lines for the calcined material are shown in table 5 below.

TABLE 5

| Example 5 ||| Example 5 calcined |||
|---|---|---|---|---|---|
| 2-Θ | d(Å) | $I/I_0$ % | 2Θ | d(Å) | $I/I_0$ % |
| 8.74 | 10.11 | m | 8.64 | 10.23 | m |
| 11.02 | 8.02 | m | 10.92 | 8.10 | vs |
| 11.70 | 7.56 | w | 11.57 | 7.64 | w |
| 13.52 | 6.54 | m | 13.42 | 6.59 | vs |
| 16.12 | 5.50 | w | 16.02 | 5.53 | w |
| 17.50 | 5.07 | s | 17.34 | 5.11 | m |
| 17.92 | 4.95 | w | 17.74 | 5.00 | w |
| 21.10 | 4.21 | m | 20.86 | 4.26 | m |
| 22.16 | 4.01 | vs | 22.00 | 4.04 | m |
| 23.54 | 3.78 | m | 23.38 | 3.80 | w |
| 25.12 | 3.54 | w | 24.90 | 3.57 | w |
| 27.22 | 3.27 | m | 27.08 | 3.29 | w |
| 28.66 | 3.11 | m | 28.36 | 3.14 | m |
| 29.45 | 3.03 | w | 29.24 | 3.05 | w |
| 31.82 | 2.81 | w | 31.46 | 2.84 | w |
| 32.54 | 2.75 | m | 32.32 | 2.77 | m |
| 34.70 | 2.58 | w | 34.36 | 2.61 | w |
| 35.36 | 2.54 | w | 35.18 | 2.55 | w |
| 36.26 | 2.48 | w | 36.12 | 2.49 | w |
| 42.36 | 2.13 | w | 42.02 | 2.15 | w |
| 43.10 | 2.10 | w | 42.72 | 2.12 | w |
| 44.64 | 2.03 | w | 44.90 | 2.02 | w |
| 45.20 | 2.00 | w | 47.54 | 1.91 | w |
| 48.16 | 1.89 | w | 48.58 | 1.87 | w |
| 49.05 | 1.86 | w | 49.24 | 1.85 | w |
| 50.23 | 1.81 | w | 49.96 | 1.82 | w |
| 51.80 | 1.76 | w | 51.30 | 1.78 | w |
| 55.68 | 1.65 | w | | | |

EXAMPLE 6

A Teflon beaker was charged with 130.00 g DEDMAOH (20%) to which 7.46 g Ludox AS-40™ colloidal silica (40% silica) was added. The mixture was placed in a Teflon bottle, sealed and digested in an oven at 95° C. for 1.5 hours. The resulting solution transferred to a beaker, placed under a high speed mixer, and with vigorous stirring, 44.63 g $Al(OsecBu)_3$ (97%) was added in 5 pours. The clear solution was stirred for an hour. Next, 25.15 g $H_3PO_4$ (85%) was added dropwise and intermittently. The solution became warm and a little cloudy. After 90 minutes of post-addition stirring, the reaction mixture was distributed among 6 Teflon-lined autoclaves and digested at autogenous pressure at a variety of temperatures and time periods. The products were isolated by centrifugation, washed with de-ionized water, and dried at room temperature. All of the products were identified as SAPO-67 based on their x-ray diffraction patterns. The characteristic diffraction lines for the product isolated from the 175° C./38 hour digestion are shown in Table 6 below.

TABLE 6

| 2-Θ | d(Å) | I/I$_0$ % |
|---|---|---|
| 8.58 | 10.30 | w |
| 10.90 | 8.11 | m |
| 11.60 | 7.62 | w |
| 13.28 | 6.66 | m |
| 15.84 | 5.59 | w |
| 17.24 | 5.14 | s |
| 17.68 | 5.01 | w |
| 20.94 | 4.24 | m |
| 21.82 | 4.07 | vs |
| 22.62 | 3.93 | w |
| 23.15 | 3.84 | m |
| 23.38 | 3.80 | w |
| 24.90 | 3.57 | w |
| 26.80 | 3.32 | m |
| 28.48 | 3.13 | m |
| 29.02 | 3.07 | w |
| 31.56 | 2.83 | w |
| 32.04 | 2.79 | m |
| 34.38 | 2.61 | w |
| 34.86 | 2.57 | w |
| 35.42 | 2.53 | w |
| 35.71 | 2.51 | w |
| 36.91 | 2.43 | w |
| 37.66 | 2.39 | w |
| 39.27 | 2.29 | w |
| 40.69 | 2.22 | w |
| 41.89 | 2.15 | w |
| 42.28 | 2.14 | w |
| 42.78 | 2.11 | w |
| 47.90 | 1.90 | w |
| 48.40 | 1.88 | w |
| 49.42 | 1.84 | w |
| 51.20 | 1.78 | w |
| 55.03 | 1.67 | w |
| 55.25 | 1.66 | w |

EXAMPLE 7

A Teflon beaker was charged with 130.00 g ETMAOH (20%) and placed under a high speed stirrer. With vigorous stirring, 6.29 g Al(OH)$_3$ (85.1%) was added slowly, forming a cloudy suspension. This was followed by the dropwise addition of 33.25 g H$_3$PO$_4$ (85%) and further homogenization that yielded a white homogenous reaction mixture. Separately, 2.94 g Mg(OAc)$_2$*4H$_2$O was dissolved in 10.30 g de-ionized water. This solution was added dropwise. Near the end of the addition the reaction mixture became a thick gel. The gel thinned out with some very high speed stirring and the resulting smooth white gel was homogenized further with normal stirring. The reaction mixture was distributed among 8 Teflon-lined autoclaves and digested at autogenous pressure at a variety of temperatures and time periods. The reaction products were isolated by centrifugation, washed with de-ionized water and dried at room temperature. The reaction mixtures digested at 125 and 150° C. yielded products identified as MAPO-67 by powder x-ray diffraction. Characteristic diffraction lines for the product from a 125° C./155 hour digestion are given below in Table 7. A portion of this material was calcined at 500° C., using a ramp rate of 2° C./min in a nitrogen atmosphere, calcining in nitrogen for 4 hours before switching to dry air and calcining for an additional 2 hours at 500° C. The material was identified as AlPO-67C by powder x-ray diffraction. The diffraction lines for the calcined material are shown in table 7 below.

TABLE 7

| Example 7 | | | Example 7 calcined | | |
|---|---|---|---|---|---|
| 2-Θ | d(Å) | I/I$_0$ % | 2-Θ | d(Å) | I/I$_0$ % |
| 8.65 | 10.22 | w | 8.68 | 10.18 | 8.68 |
| 10.91 | 8.11 | m | 10.96 | 8.07 | 10.96 |
| 11.55 | 7.66 | w | 11.56 | 7.65 | 11.56 |
| 13.42 | 6.59 | m | 13.5 | 6.55 | 13.5 |
| 15.98 | 5.54 | w | 16.11 | 5.5 | 16.11 |
| 17.33 | 5.11 | s | 17.4 | 5.09 | 17.4 |
| 17.75 | 4.99 | w | 20.9 | 4.25 | 20.9 |
| 20.82 | 4.26 | m | 22.14 | 4.01 | 22.14 |
| 21.98 | 4.04 | vs | 23.28 | 3.82 | 23.28 |
| 22.74 | 3.91 | w | 23.59 | 3.77 | 23.59 |
| 23.36 | 3.81 | m | 24.98 | 3.56 | 24.98 |
| 24.88 | 3.58 | w | 27.16 | 3.28 | 27.16 |
| 27.02 | 3.30 | w | 28.38 | 3.14 | 28.38 |
| 28.34 | 3.15 | m | 31.57 | 2.83 | 31.57 |
| 29.25 | 3.05 | w | 32.46 | 2.76 | 32.46 |
| 31.44 | 2.84 | w | 34.47 | 2.6 | 34.47 |
| 32.30 | 2.77 | m | | | |
| 34.34 | 2.61 | w | | | |
| 35.13 | 2.55 | w | | | |
| 36.04 | 2.49 | w | | | |
| 39.65 | 2.27 | w | | | |
| 41.94 | 2.15 | w | | | |
| 42.64 | 2.12 | w | | | |
| 44.88 | 2.02 | w | | | |
| 47.55 | 1.91 | w | | | |
| 48.53 | 1.87 | w | | | |
| 49.16 | 1.85 | w | | | |
| 49.85 | 1.83 | w | | | |
| 51.18 | 1.78 | w | | | |
| 55.10 | 1.67 | w | | | |
| 55.77 | 1.65 | w | | | |

EXAMPLE 8

A Teflon bottle was charged with 130.00 g ETMAOH (20%) and 6.19 g LUDOX AS-40™ colloidal silica (40% SiO$_2$), stirred briefly, sealed and placed in a 95° C. oven for 2 hours. The resulting solution was placed in a Teflon beaker under a high speed stirrer. Began adding 6.29 g Al(OH)$_3$ (85.1%) slowly with vigorous stirring. The resulting cloudy suspension was homogenized for an additional 45 minutes one the addition was complete. Then 28.50 g H$_3$PO$_4$ (85%) was added dropwise and intermittently in 5 separate portions, resulting in a semi-transparent homogeneous reaction mixture. Separately, 3.01 g Zn(OAc)$_2$*2H$_2$O was dissolved in 12.0 g de-ionized water. This solution was added dropwise intermittently in three separate portions. The opaque reaction mixture was distributed among 7 Teflon-lined autoclaves and digested at autogenous pressure at a variety of temperatures and time periods. The reaction products were isolated by centrifugation, washed with de-ionized water and dried at room temperature. The products from the 125, 150 and 175° C. digestions were identified as MAPSO-67 via powder x-ray diffraction. Characteristic diffraction lines for the product from the 175° C./182 hour digestion are given in Table 8 below.

TABLE 8

| 2-Θ | d(Å) | I/I₀ % | |
|---|---|---|---|
| 8.52 | 10.37 | w | br |
| 10.67 | 8.29 | m | br |
| 13.32 | 6.64 | vs | |
| 17.26 | 5.13 | m | br |
| 21.00 | 4.23 | m | sh |
| 21.82 | 4.07 | s | br |
| 23.18 | 3.83 | s | |
| 26.82 | 3.32 | m | |
| 28.49 | 3.13 | m | br |
| 28.88 | 3.09 | m | sh |
| 32.06 | 2.79 | m | br |
| 49.44 | 1.84 | w | |
| 50.94 | 1.79 | m | | br = broad, sh = shoulder

EXAMPLE 9

A Teflon bottle was charged with 130.00 g ETMAOH (20%) and 6.19 g LUDOX AS-40™ colloidal silica (40% SiO₂), stirred briefly, sealed and placed in a 95° C. oven for 90 minutes. The resulting solution was placed in a Teflon beaker under a high speed stirrer. Began adding 6.29 g Al(OH)₃ (85.1%) slowly and intermittently in 5 separate portions. The resulting cloudy suspension was homogenized. Then 28.50 g H₃PO₄ (85%) was added dropwise and intermittently, resulting in a homogeneous opalescent reaction mixture. Separately, 1.51 g Zn(OAc)₂*2H₂O was dissolved in 6.00 g de-ionized water. This solution was added dropwise intermittently in three separate portions. The opaque reaction mixture was distributed among 7 Teflon-lined autoclaves and digested at autogenous pressure at a variety of temperatures and time periods. The reaction products were isolated by centrifugation, washed with de-ionized water and dried at room temperature. The products from the 125, 150 and 175° C. digestions were identified as MAPSO-67 via powder x-ray diffraction. Characteristic diffraction lines for the product from the 175° C./42 hour digestion are given in Table 9 below.

TABLE 9

| 2-Θ | d(Å) | I/I₀ % | |
|---|---|---|---|
| 8.52 | 10.37 | w | br |
| 10.92 | 8.10 | m | br |
| 13.36 | 6.62 | vs | |
| 15.84 | 5.59 | w | sh |
| 17.26 | 5.13 | s | |
| 20.88 | 4.25 | m | sh |
| 21.96 | 4.04 | vs | br |
| 23.26 | 3.82 | s | |
| 26.86 | 3.32 | m | |
| 28.48 | 3.13 | m | br |
| 28.96 | 3.08 | m | sh |
| 32.22 | 2.78 | m | |
| 34.50 | 2.60 | w | |
| 35.82 | 2.50 | w | |
| 42.51 | 2.12 | w | |
| 51.01 | 1.79 | m | |
| 55.56 | 1.65 | w | | br = broad, sh = shoulder

EXAMPLE 10

A Teflon bottle was charged with 150.00 g DEDMAOH (20%) and 7.56 g LUDOX AS-40™ colloidal silica (40% SiO₂), stirred briefly, sealed and placed in a 95° C. oven for 2 hours. The resulting solution was placed in a Teflon beaker under a high speed stirrer. Began adding 41.83 g Al(OsecBu)₃ (10.9% Al) slowly resulting in a clear solution immediately. Then 23.98 g H₃PO₄ (85.7%) was added dropwise and intermittently, resulting in a clear solution with some separation of sec-BuOH formed during the hydrolysis. The reaction mixture was allowed to homogenize further. The reaction mixture was then distributed among two Teflon-lined autoclaves and digested at autogenous pressure at 175° C. for 61 hours. The reaction products were isolated by centrifugation, washed with de-ionized water and dried at room temperature. The products were identified as SAPO-67 via powder x-ray diffraction. Characteristic diffraction lines for the product are given in Table 10 below. A portion of this material was calcined at 500° C. first in nitrogen and then in air. The sample was ramped to 500° C. at 2° C./min in nitrogen and then calcined for 4 hours in nitrogen. While the temperature remained at 500° C., the atmosphere was switched to air and the material was calcined for another two hours. The material was identified as AlPO-67C via powder x-ray diffraction. The characteristic diffraction lines for the product are shown in Table 10 below.

TABLE 10

| Example 10 | | | Example 10 calcined | | |
|---|---|---|---|---|---|
| 2-Θ | d(Å) | I/I₀ % | 2Θ | d(Å) | I/I₀ % |
| 8.58 | 10.30 | w | 8.82 | 10.01 | w |
| 10.84 | 8.16 | m | 11.00 | 8.04 | vs |
| 13.32 | 6.64 | m | 13.60 | 6.51 | vs |
| 15.86 | 5.58 | w | 17.38 | 5.1 | m |
| 17.20 | 5.15 | s | 21.04 | 4.22 | m |
| 17.80 | 4.98 | w | 22.1 | 4.02 | s |
| 21.10 | 4.21 | m | 23.53 | 3.78 | m |
| 21.80 | 4.07 | vs | 25.13 | 3.54 | w |
| 23.14 | 3.84 | m | 27.12 | 3.29 | m |
| 25.01 | 3.56 | w | 28.58 | 3.12 | m |
| 26.78 | 3.33 | m | 29.36 | 3.04 | w |
| 28.52 | 3.13 | m | 31.64 | 2.83 | w |
| 28.94 | 3.08 | w | 32.30 | 2.77 | m |
| 30.98 | 2.88 | w | 34.54 | 2.6 | w |
| 31.62 | 2.83 | w | 35.28 | 2.54 | w |
| 31.98 | 2.80 | m | 42.72 | 2.11 | w |
| 34.42 | 2.60 | w | 51.28 | 1.78 | w |
| 34.74 | 2.58 | w | | | |
| 35.40 | 2.53 | w | | | |
| 35.66 | 2.52 | w | | | |
| 40.64 | 2.22 | w | | | |
| 41.90 | 2.15 | w | | | |
| 42.70 | 2.12 | w | | | |
| 44.17 | 2.05 | w | | | |
| 44.42 | 2.04 | w | | | |
| 48.33 | 1.88 | w | | | |
| 48.66 | 1.87 | w | | | |
| 49.34 | 1.85 | w | | | |
| 51.10 | 1.79 | w | | | |
| 55.18 | 1.66 | w | | | |

What is claimed is:

1. A hydrocarbon conversion process for the alkylation of aromatics comprising contacting a stream comprising aromatic compounds with an alkylating agent with a catalyst at hydrocarbon conversion conditions to generate at least one alkylated aromatic compound, wherein the catalyst comprises a microporous crystalline AlPO-67 material, where AlPO-67 has a three-dimensional framework of $EO_2^-$, $PO_2^+$ and at least one of $[M^{2+}O_2]^{2-}$ and $SiO_2$ tetrahedral units and an empirical composition in the as synthesized and anhydrous basis expressed by an empirical formula of:

$$R_r M_m^{2+} E P_x Si_y O_z$$

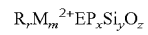

where M is at least one framework cation of valence 2+ selected from the group consisting of alkaline earth and transition metals, "m" is the mole ratio of M to E and varies from 0 to about 1.0, R is an organoammonium cation selected from the group of ethyltrimethylammonium (ETMA$^+$), diethyldimethylammonium (DEDMA$^+$), and mixtures thereof, "r" is the mole ratio of R to E and has a value of about 0.1 to about 2.0, E is a trivalent element selected from the group consisting of aluminum, gallium, iron, boron and mixtures thereof, "x" is the mole ratio of P to E and varies from 0.5 to about 2.0, "y" is the mole ratio of Si to E and varies from 0 to about 1.0, "m"+"y"≥0.02, and "z" is the mole ratio of O to E and has a value determined by the equation:

$$z=(2\cdot m+r+3+5\cdot x+4\cdot y)/2$$

and is characterized in that it has the x-ray diffraction pattern having at least the d-spacings and intensities set forth in Table A1:

TABLE A1

| 2Θ | d(Å) | I/I$_0$ % |
|---|---|---|
| 8.86-8.39 | 9.97-10.53 | w-m |
| 11.21-10.51 | 7.89-8.41 | m-s |
| 13.65-13.16 | 6.48-6.72 | m-vs |
| 17.72-16.91 | 5.00-5.24 | m-vs |
| 21.29-20.69 | 4.17-4.29 | m-s |
| 22.43-21.5 | 3.96-4.13 | s-vs |
| 23.84-22.84 | 3.73-3.89 | w-vs |
| 27.51-26.51 | 3.24-3.36 | w-m |
| 29.06-27.95 | 3.07-3.19 | w-m |
| 32.90-31.59 | 2.72-2.83 | m |
| 35.02-33.93 | 2.56-2.64 | w-m |

TABLE A1-continued

| 2Θ | d(Å) | I/I$_0$ % |
|---|---|---|
| 36.65-35.31 | 2.45-2.54 | w-m |
| 52.23-50.67 | 1.75-1.80 | w-m. |

2. The process of claim 1 further comprising removing an effluent comprising the at least one converted product, fractionating the effluent, and recovering at least one converted product.

3. The process of claim 2 further comprising, subjecting the effluent to partial condensation and vapor-liquid separation prior to fractionation.

4. The process of claim 2 further comprising recycling at least a portion of the effluent to the catalyst.

5. The process of claim 1 wherein the hydrocarbon conversion process comprises two stage operation and the catalyst is present in at least one of the two stages.

6. The process of claim 1 wherein the hydrocarbon conversion process is alkylation of aromatics and the converted product is at least one linear alkyl substituted aromatic, and wherein the process is operated at an aromatic:olefin mole ratio of between 5:1 and 30:1, a LHSV of about 0.3 to about 6 hr$^{-1}$, a temperature of about 100° to about 250° C. and a pressures of about 200 to about 1000 psig.

7. The process of claim 1 wherein the catalyst is located in one or more catalyst zones arranged in series or parallel configuration, and wherein the catalyst may be in fixed beds or fluidized beds.

8. The process of claim 1 further comprising regenerating the catalyst.

\* \* \* \* \*